United States Patent [19]

Lipp

[11] Patent Number: 4,817,642

[45] Date of Patent: Apr. 4, 1989

[54] DENTAL FLOSS ADAPTER

[76] Inventor: Don Lipp, 585 West End Ave., New York, N.Y. 10024

[21] Appl. No.: 129,243

[22] Filed: Dec. 7, 1987

[51] Int. Cl.$^4$ ............................................. A61C 15/00
[52] U.S. Cl. .................................................... 132/324
[58] Field of Search ........................ 132/91, 92, 90, 89

[56] References Cited

U.S. PATENT DOCUMENTS

| 695,092 | 3/1902 | Cowan | 132/92 R |
|---|---|---|---|
| 1,488,214 | 3/1924 | Mason | 132/92 R |
| 1,506,417 | 8/1924 | Donals | 132/91 |
| 1,537,853 | 5/1925 | Mason | 132/84 A |
| 4,706,694 | 11/1987 | Lambert | 132/91 |

Primary Examiner—Robert Peshock
Attorney, Agent, or Firm—Charles E. Temko

[57] ABSTRACT

A dental floss and tape holder adapted to be positioned on the free end of a toothbrush handle in a hollow socket. An opposite end of the device supports a bow-shaped holder adjustably carried for relative movement to approximately 45° in either direction from the plane of the part containing the socket to facilitate engagement with the teeth of a user. A pivoted joint to accomplish this movement is configured to provide rigidity and resistance to stress.

4 Claims, 1 Drawing Sheet

DENTAL FLOSS ADAPTER

BACKGROUND OF THE INVENTION

This invention relates generally to the field of dental floss holders, and more particularly to improved form thereof of expendable type adapted to be positioned on the free end of a toothbrush handle to provide means for projecting the same into the mouth of a user.

The most common type of dental floss holder includes a bowed support, the free ends of which engage the ends of a short length of dental floss or tape which is retained at a tension sufficient to permit flossing the same between the teeth prior to longitudinal movement to effect the cleaning action. Such devices normally require a handle to provide sufficient length to enable reaching the rearwardly disposed molars.

Early types of flosses were developed during the 1920's and were equipped to carry a spool of dental floss which could be advanced to operative positions as previously used segments became worn or broken. Most early devices were made of metal, and in addition to being expensive, were relatively complicated to manufacture and clumsy in use.

With the later advent of synthetic resinous materials and molding techniques to employ them, some later devices were made of these materials. However, the devices remained relatively large in size, complicated to use, and expensive to produce.

SUMMARY OF THE INVENTION

Briefly stated, the invention contemplates the provision of an improved dental floss holder of the class described in which the above-mentioned disadvantages have been substantially eliminated.

To this end, I have provided a small disposable dental floss holder of bow type, the size of which is sufficient to allow convenient insertion by a user and capable of reaching the innermost teeth on the jaw without difficulty. A short floss or tape segment is insert molded with the supporting bow, the bow being in turn movably interconnected to a hollow member in turn selectively connected to a free end of a toothbrush handle. A bow is selectively positionable in any of several angular positions to enable it to be properly oriented for engagement between the teeth irrespective of the location thereof in the jaw of the user. Normally a 45° angle from the plane of the socket in either of two pivotal directions is adequate to accommodate for upper and lower, right and left parts of a jaw.

BRIEF DESCRIPTION OF THE DRAWING

In the drawing, to which reference will be made in the specification, similar reference characters have been employed to designate corresponding parts throughout the several views.

DETAILED DESCRIPTION OF THE DISCLOSED EMBODIMENT

Figure 1:
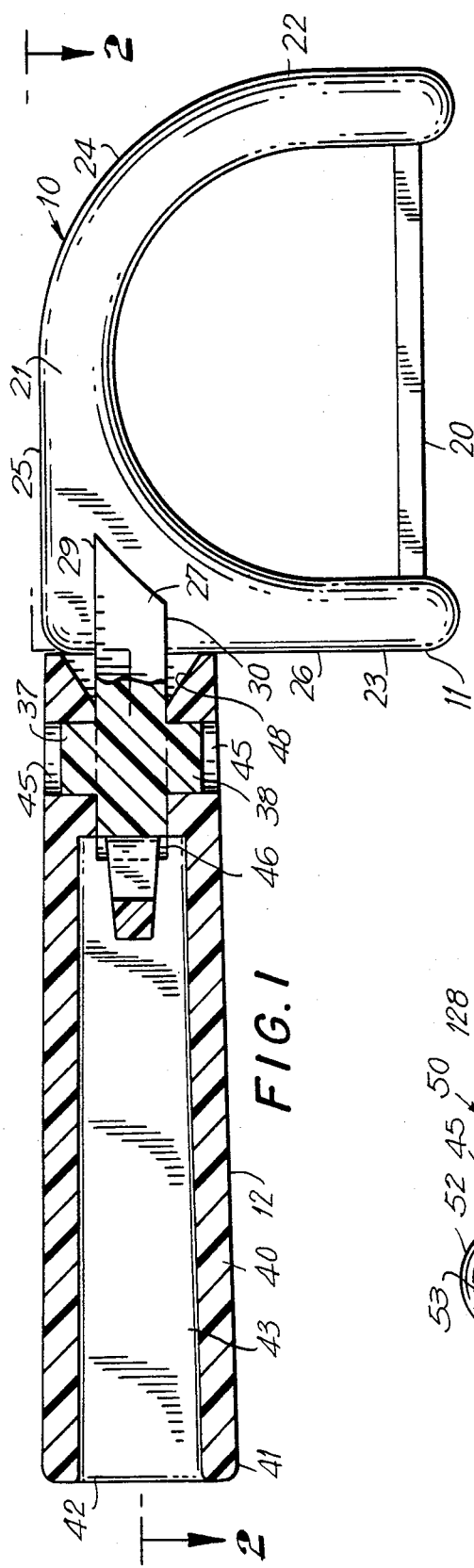
FIG. 1 is a side elevational view of an embodiment of the invention, partially broken away to show detail.

In accordance with the first embodiment of the invention, the device, generally indicated by reference character 10, comprises broadly: a floss holding or supporting element 11 and a handle-engaging element 12.

The element 11 is most conveniently formed as a synthetic resinous molding, and includes an insert molded short length of floss or tape 20. The element 11 includes a main body 21 forming first and second arms 22 and 23 constituting a bow. The bow is bounded by a curved upper surface 24 merging with a planar surface 25 at the upper portion thereof. Extending from a transverse surface 26 is an integrally molded interconnecting member 27 including a generally planar body 28 bounded by upper and lower surfaces 29 and 30, converging side surfaces 31 and 32 and a rounded surface 33. The surface 33 includes plural detent recesses 35, 35 and 36. Extending from the surfaces 29 and 30, respectively, are cylindrical upper and lower projections 37 and 38, the axis of which forms a pivot axis for the element 11 with respect to the element 12.

The element 12 is also conveniently formed as a synthetic resinous molding, and includes an elongated hollow tube 40, a first end 41 of which provides an opening 42 to a hollow tapered socket 43 selectively engageable with the free end of a toothbrush or the like. A second end 44 thereof is of rounded configuration and includes a transversely extending through bore 45, the center of which intersects a circular planar recess 46 which accommodates the body 28. Camming surfaces 47 and 48 permit the second end 44 to be spread upon engaging the ends of the projections 37 and 38 so that the projections can be snapped into the bore 45 during assembly. An integrally molded detent member 49 selectively engages any of the recesses 34, 35 and 36 to maintain the angular adjustment between the elements 11 and 12.

Use of the device is readily understood from a consideration of the drawing. Each device, as the floss segment becomes worn or broken, may be readily disconnected from the end of the toothbrush handle (not shown), to be replaced by another device. Normally, the forward teeth, including the incisors, can be conveniently flossed with the element 11 in coplanar relation with respect to the element 12, the upper and lower teeth being accommodated by merely rotating the device about its own principal axis through 180°.

The rear teeth are accommodated by moving the element 11 through 45° on either side of the element 12 which will provide access without excessive torque tending to loosen the projections 37 and 38. One adjustment will accommodate the lower teeth on one side of the jaws and the upper teeth on the other side, and the other adjustment accommodates the remaining teeth.

Figure 3:
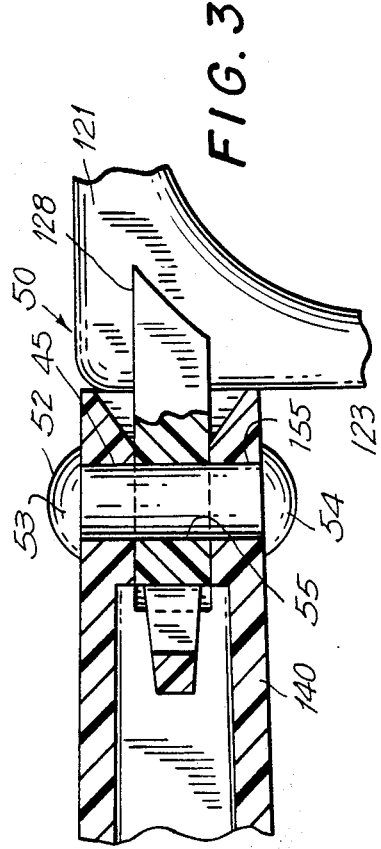
FIG. 3 is a side elevational view, corresponding to that seen in FIG. 1, but showing a second embodiment of the invention.
Figure 2:
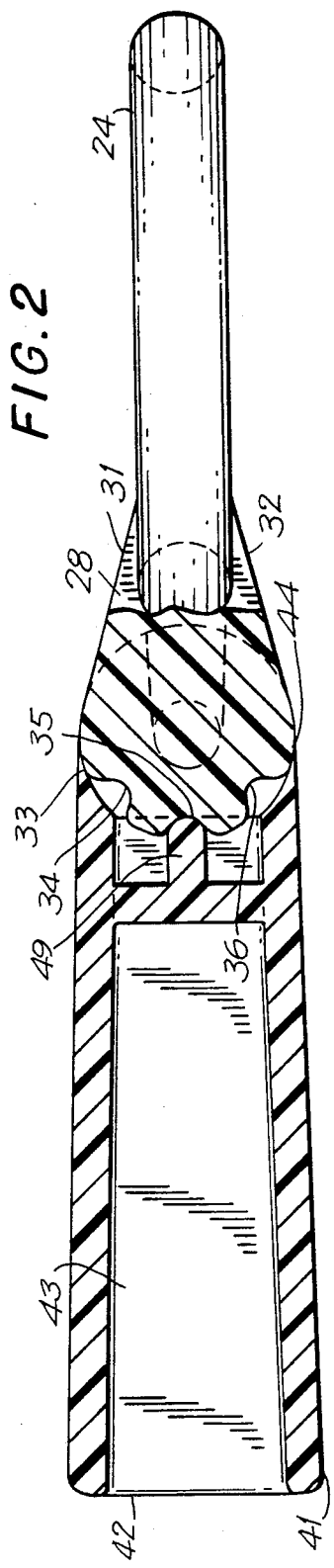
FIG. 2 is a top plan view thereof, also partially broken away to show detail.

Turning now to the second embodiment of the invention, generally indicated by reference character 50, and illustrated in FIG. 3 in the drawing, parts corresponding to those of the principal embodiment have been designated by similar reference characters with the additional prefix "1".

In the second embodiment, the projections 37 and 38 of the first embodiment are replaced by a synthetic resinous or metallic pintle 52, which permits the illumination of the camming surfaces 47 and 48 as well. The pintle 52 includes headed enlargements 53 and 54, one of which is formed prior to assembly, and the other formed after it has penetrated the bore 145 and bore 55 in the planar body 128. It will be appreciated that this embodiment affords far greater mechanical strength at the pivot axis without substantially complicating assembly.

I wish it to be understood that I do not consider the invention to be limited to the precise details of structure as shown and set forth in the specification, for obvious modifications will occur to those skilled in the art to which the invention pertains.

I claim:

1. A disposable dental floss holder adapted to be supported upon a free end of a handle of a toothbrush comprising: a floss supporting element and a handle engaging element pivotally interconnected therewith; said floss supporting element having a main body of bowed configuration, including first and second free ends, an insert-molded length of dental floss extending between said free ends, an interconnecting member integrally molded with said main body and including a generally planar body extending laterally therefrom, said planar body having an arcuate peripheral surface having plural detent recesses therein, pivot means extending from said body having a principal axis perpendicular to that of said planar body; said handle-engaging element forming an elongated hollow tube open at a first end thereof to define a socket for engaging a free end of a toothbrush, and a second end having a planar recess corresponding in configuration to that of said planar body, and defining a continuous bore having an axis perpendicular to said planar recess pivotally engaging said pivot means, said planar recess including detent means selectively engageable with one of said detent recesses; whereby said floss supporting element may be selectively positioned at a desired angle relative to the axis of said handle-engaging element.

2. A dental floss holder in accordance with claim 1, further characterized in said pivot means comprising a pair of integrally molded projections on said planar body.

3. A dental floss holder in accordance with claim 1, further characterized in said pivot means comprising an elongated shaft penetrating said floss supporting element and said handle engaging element.

4. A dental floss holder in accordance with claim 3, further characterized in said elongated shaft projecting outwardly of said handle-engaging element, and having an enlargement at each free end thereof.

* * * * *